United States Patent
Nakayama

(10) Patent No.: US 7,111,784 B2
(45) Date of Patent: Sep. 26, 2006

(54) COLOR IMAGE FORMING APPARATUS AND COLOR MEASUREMENT CONTROLLING METHOD THEREFOR

(75) Inventor: Toshiki Nakayama, Shizuoka (JP)

(73) Assignee: Canon Kabushiki Kaisha, Tokyo (JP)

( * ) Notice: Subject to any disclaimer, the term of this patent is extended or adjusted under 35 U.S.C. 154(b) by 147 days.

(21) Appl. No.: 10/772,359

(22) Filed: Feb. 6, 2004

(65) Prior Publication Data

US 2004/0156047 A1 Aug. 12, 2004

(30) Foreign Application Priority Data

Feb. 12, 2003 (JP) .............................. 2003-033516

(51) Int. Cl.
*G06K 7/10* (2006.01)

(52) U.S. Cl. .............................. 235/462.04; 235/462.25

(58) Field of Classification Search ........... 235/462.04, 235/462.25, 436, 454; 399/39, 45, 47
See application file for complete search history.

(56) References Cited

U.S. PATENT DOCUMENTS 6,614,530 B1 * 9/2003 Duez et al. ................. 356/406
6,731,889 B1 * 5/2004 Nakayama .................... 399/49
6,750,892 B1 * 6/2004 Suzuki ........................ 347/133
6,784,994 B1 * 8/2004 Kritchman et al. ......... 356/402
6,898,381 B1 * 5/2005 Maebashi et al. ............. 399/15
2001/0024285 A1 9/2001 Kondo ........................ 358/1.1
2003/0044190 A1 3/2003 Nakayama .................... 399/49

FOREIGN PATENT DOCUMENTS

JP 2001-273508 A 10/2001
JP 2001-297068 A 10/2001

* cited by examiner

*Primary Examiner*—Daniel St. Cyr

(57) ABSTRACT

A color image forming apparatus, when a white LED is made to emit light onto a color image so that the reflected light can be detected, changes a color measuring condition in adaptation to a reflectance predicted for the image from the forming condition of the color image to be detected. The amount of reflected light is detected by photodiodes, and the image forming condition is adjusted, based on the detected amount of reflected light of each color image. Thereby, irrespective of the reflectance of each color image, the color measurement of each color image is effected with good accuracy, and the hue and density of the color image to be detected are accurately detected, thereby to form a color image with excellent color reproduction.

30 Claims, 12 Drawing Sheets

FIG. 12
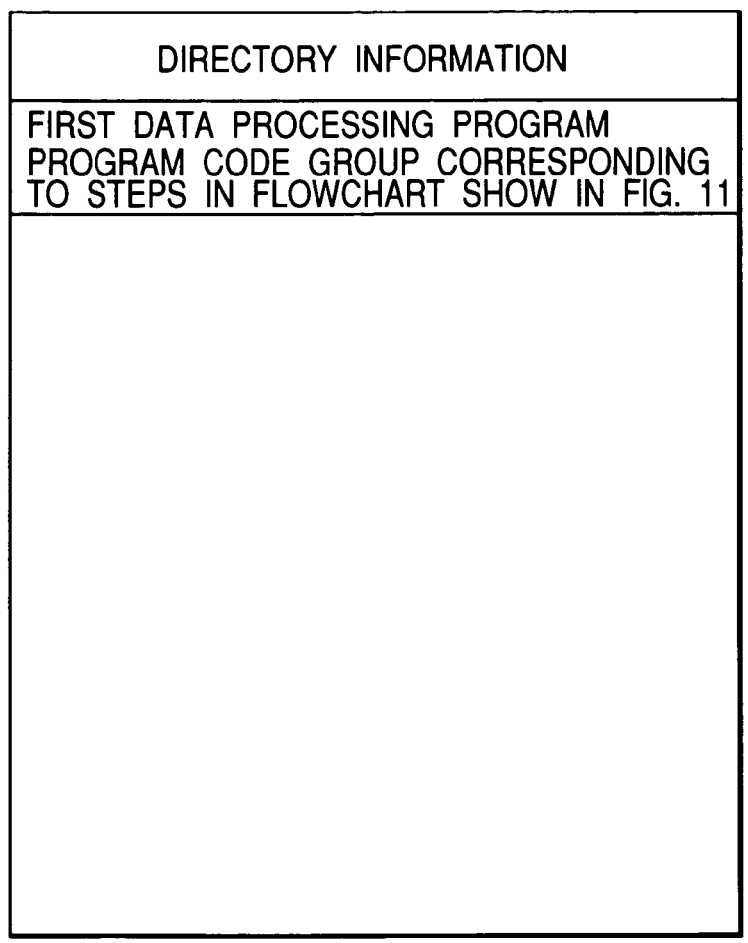
| DIRECTORY INFORMATION |
|---|
| FIRST DATA PROCESSING PROGRAM PROGRAM CODE GROUP CORRESPONDING TO STEPS IN FLOWCHART SHOW IN FIG. 11 |
FIG. 13A          FIG. 13B
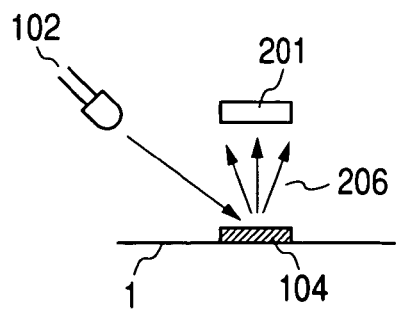
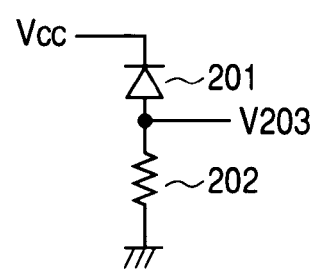

COLOR IMAGE FORMING APPARATUS AND COLOR MEASUREMENT CONTROLLING METHOD THEREFOR

BACKGROUND OF THE INVENTION

1. Field of the Invention

This invention relates to a color image apparatus capable of forming a color image, such as a copying machine or a printer of an electrophotographic type, an electrostatic memory type or the like provided with a color measuring apparatus for automatically color-measuring an output image, a color measurement controlling method for the color image forming apparatus, and a storage medium and a program capable of being read by a computer.

2. Related Background Art

There has heretofore been a case where a color image forming apparatus or the like is provided with a color measuring apparatus for detecting image information from an image formed by the apparatus.

FIGS. 13A and 13B of the accompanying drawings illustrate the construction of a color measuring apparatus which can be utilized in a color image forming apparatus of this kind. FIG. 13A shows an example of the image detection thereof, and FIG. 13B shows an example of an image detection circuit (a circuit for converting the output current of a photodiode into a voltage). This example is an example of a sensor using a photodiode to detect reflected light from a toner.

In FIG. 13A, the reference numeral 201 designates a photodiode (sensor), and the reference numeral 102 denotes an LED which serves as a light source and which, as described below, illuminates a patch of toner with a constant amount of light.

The reference numeral 104 designates a toner patch which is an object of detection formed on a conveyed transferring material 1, and reflected light 206 from this toner patch 104 enters the photodiode 201, whereby a photocurrent is generated. The photocurrent is converted into a photoelectric conversion output (voltage signal) V203 by a resistor 202.

This photoelectric conversion output V203 reflects the amount of reflected light from the surface of a toner patch, in real time. A color measuring apparatus can be formed by a sensor using such a photodiode.

Specifically, as the LED light source 102, three LEDs of for example red (R), green (G) and blue (B), differing in light emission spectrum from one another, are provided to serve as light sources of respective colors, and the respective LEDs are caused to emit light independently of one another onto the toner patch which is the object of measurement, and the output of the sensor corresponding to each LED is obtained, whereby there can be obtained the R, G and B components of reflected light from the toner patch, and chromaticity such as L*a*b* or XYZ in color space processing or the like can be calculated.

FIG. 14 of the accompanying drawings is a block diagram showing the pixel construction of a line sensor of an accumulation type utilized in a conventional color image forming apparatus.

The reference numeral 204 denotes a sensor array comprising pixels 207 to 220. The reference numeral 205 designates a reading-out circuit, and the reference numeral 206 denotes a reset circuit. The pixels 207 to 209 and 220 are pixels of which the surfaces are shielded from light. The pixels 210 to 219 are a row of pixels responding to light.

The pixels 207 and 220 serve also as dummy pixels absorbing the unevenness of a sensor characteristic by their being located at the end portions.

Here, for simplicity, an example having ten pixels responding to light is described, but in practice the number of effective pixels is determined according to need. As the dark pixels, there has been shown an example in which there are 3 bits in the first half and 1 bit in the second half, but again the number of bits is increased or decreased depending on the degree of leakage of light between the pixels and the requirements of the particular actual system.

FIG. 15 of the accompanying drawings is a timing chart illustrating the operation timing of the line sensor of the accumulation type shown in FIG. 14.

First, a reset pulse 221 is applied to a port P1, thereby to reset the sensor 201, after which the reset is released and accumulation is started. During the accumulation, the accumulation capacitance (not shown) of the sensor 201 is charged with a photocurrent conforming to the amount of incident light.

However, the bits shielded from light have their accumulation capacitance charged with a dark current generated by the pixel portion. After accumulation for a predetermined time ta, a forwarding pulse 222 is applied to a port P2, whereupon the output of the sensor 201 is collectively forward to the reading-out circuit 205, and is outputted as an output signal 224 from a port P4 for each pixel on the basis of a shift pulse 223 inputted by a shift register in the reading-out circuit 205 through a port P3.

At this time, an output corresponding to the dark pixel 208 is defined as a dark time output and is subtracted from the outputs of the subsequent effective pixels, whereby there is obtained a signal in which an error due to the dark current of the sensor 201 has been corrected. The color measuring apparatus can also be formed by such a cumulative type sensor.

Specifically, for example, R, G and B filters are provided on the surface of the sensor, and the toner patch which is the object of measurement is illuminated by a light source like a white LED having a spectrum over the entire visible light area, and the output of the sensor 201 corresponding to each filter is obtained, whereby the R, G and B components of reflected light from the toner patch are obtained, and chromaticity such as L*a*b* or XYZ in the above-mentioned color space processing can be calculated.

FIG. 16 of the accompanying drawings is a schematic cross-sectional view illustrating the construction of a color image forming apparatus of this kind, and corresponds, for example, to the case of a four-set tandem type color laser printer.

Also, the color laser printer forms an electrostatic latent image by image light formed on the basis of an image signal in an image forming portion, develops this electrostatic latent image to form a visible image, further transfers this color visible image to a transferring material (a recording medium), and then fixes the color visible image.

In FIG. 16, the image forming portion is comprised of photosensitive drums 5Y, 5M, 5C, 5K, injection charging devices 7Y, 7M, 7C, 7K as primary charging means, developing devices 8Y, 8M, 8C, 8K and toner cartridges 11Y, 11M, 11C, 11K in respective stations juxtaposed by the number of developing colors, an intermediate transferring member 12, a sheet feeding portion, a transferring portion and a fixing portion 13.

Each of the photosensitive drums 5Y, 5M, 5C and 5K is constituted by an aluminum cylinder and an organic photoconductive layer applied to the outer periphery thereof, and is rotated by the driving force of a drive motor, not shown, being transmitted thereto, and the drive motor rotates the photosensitive drums 5Y, 5M, 5C and 5K counter-clockwise in conformity with an image forming operation.

Exposure light is sent to the photosensitive drums 5Y, 5M, 5C and 5K from scanner portions 10Y, 10M, 10C and 10K, and light from each of those scanner portions is selectively applied to the surfaces of the photosensitive drums 5Y, 5M, 5C and 5K, respectively, whereby electrostatic latent images are successively formed thereon.

As the primary charging means, provision is made of the four injection charging devices 7Y, 7M, 7C and 7K for charging the yellow (Y), magenta (M), cyan (C) and black (K) photosensitive drums in the respective stations, and the respective injection charging devices are provided with sleeves 7YS, 7MS, 7CS and 7KS.

As developing means, the four developing devices 8Y, 8M, 8C and 8K for effecting yellow (Y), magenta (M), cyan (C) and black (K) development in the respective stations are provided to visualize the above-mentioned electrostatic latent images, and the respective developing devices are provided with sleeves 8YS, 8MS, 8CS and 8KS. The respective developing devices are detachably mounted with respect to an apparatus main body.

The intermediate transferring member 12 is an endless belt member passed over a drive roller 18a and driven rollers 18b, 18c, is in contact with the photosensitive drums 5Y, 5M, 5C and 5K, is rotated clockwise during color image forming, and is sequentially subjected to transfer by the action of primary transferring rollers 6Y, 6M, 6C and 6K for the respective colors.

Transferring materials 1 are contained in a sheet feeding cassette 2 or a sheet feeding tray 3 as sheet feeding means (sheet feeding port), and the transferring materials 1 are conveyed one by one along a conveying path 25 constituted by a sheet feeding roller 4 and conveying rollers 24 and arrive at registration rollers 23. This is detected by an ante-registration sensor 19.

During image forming, the conveyance of the transferring material is stopped for a predetermined time by the ante-registration sensor 19 in timed relationship with the arrival of the color visible images on the intermediate transferring material 12 at a transferring area. The transferring material 1 is fed from the registration rollers 23 to the transferring area, and a secondary transferring roller 9 comes into contact with the intermediate transferring member 12 and nips and conveys the transferring material, thereby to superimpose and transfer the color visible images on the intermediate transferring member 12 onto the transferring material 1 one at a time.

The secondary transferring roller 9 is brought into contact with the intermediate transferring member 12 as indicated by a solid line as long as the color visible images are superimposed and transferred onto the intermediate transferring member 12, but it is brought to a spaced-apart position indicated by dotted line after the termination of the printing process.

The fixing portion 13 serves to fix the transferred color visible images while conveying the transferring material 1, and is provided with affixing roller 14 for heating the transferring material 1 and a pressure roller 15 for bringing the transferring material 1 into pressure contact with the fixing roller 14, as shown in FIGS. 13A and 13B. The fixing roller 14 and the pressure roller 15 are formed into a hollow shape, and contain heaters 16 and 17, respectively, therein. That is, the transferring member 1 bearing the color visible image thereon is conveyed by the fixing roller 14 and the pressure roller 15 and also have heat and pressure applied thereto, whereby the toners are fixed on the surface thereof.

After the fixing of the visible image, the transferring material 1 is discharged to a sheet discharging portion, not shown, by discharge rollers, not shown, thus completing the image forming operation. The discharge of the transferring material 1 from the fixing portion is detected by a fixed sheet discharge sensor 20.

Cleaning means 21 stores therein waste toners after the color visible images of the four colors formed on the intermediate transferring member 12 have been transferred to the transferring material 1.

Color misregister detecting means 22 forms a color misregister detection patch on the transferring material, detects the amounts of misregister among the colors in a main scanning direction and a sub-scanning direction, and applies feedback so as to finely adjust image data to thereby reduce color misregister.

When the above-described multicolor image forming apparatus is used, if fluctuation occurs in one or another portion of the apparatus due to a change in environment or the long-time use of the apparatus, the density and chromaticity of an image obtained will fluctuate.

Particularly, in the case of a color image forming apparatus of the electrophotographic type, even a slight density fluctuation may lead to the possibility of color balance being destroyed, and therefore, it is necessary always to keep constant density and gradation.

So, process conditions such as several kinds of exposure amounts and developing biases corresponding to absolute humidity and gradation correcting means such as a look-up table (LUT) are provided for the toner of each color, and on the basis of the absolute humidity measured by a temperature and humidity sensor, not shown, the then-applicable process conditions and gradation correction value are selected.

Also, in order that constant density, gradation and hue may be obtained even if, during the image forming process, fluctuation occurs to image forming colors in the respective portions of the apparatus with the fluctuation in environment, a toner image for density detection (hereinafter referred to as a "toner patch") is formed on the intermediate transferring member with toner of each color, and this toner patch is detected by an optical sensor disposed at a location equivalent to the detecting means 22, and from the result thereof, feedback is applied to the process conditions such as the exposure amount and the developing bias and density control is effected, thereby to obtain a stable image.

However, in a color measuring apparatus using the sensor and the controlling method according to the prior art to obtain a stable image in the multicolor image forming apparatus, the following problems have been encountered in effecting the color measurement of the toner patch on the paper after fixing.

First, in order to obtain a stable image, it is necessary to form toner patches of various chromaticities on the transferring material, actually measure those chromaticities by the above-described sensor 201 to find the difference thereof from a desired chromaticity, and apply feedback to the process conditions.

Also, the reflectance of the toner patch is not uniform but varies from a high level to a low level, and the output of the sensor 201 fluctuates from a nearly saturated output to nearly a dark-time output. In the case of a patch which is high in density and low in reflectance, the output thereof becomes small and is buried in the quantization error during the AD conversion of the signal or the noise of a reading-out system, and a correct signal cannot be obtained.

Accordingly, in the case of a patch which is low in reflectance, color measurement accuracy becomes bad, and when the result thereof is to be fed back to the image forming apparatus in an effort to achieve color stabilization, there has been the problem that conversely the hue becomes unstable.

SUMMARY OF THE INVENTION

The present invention has been made in order to solve the above-noted problems.

One aspect of the present invention is a color image forming apparatus that comprises an image forming unit which forms a color image on a recording material, and a color measuring unit that optically measures plural colors of each of plural patch images formed on a recording material by the image forming unit, by detecting reflected light of each color from each patch image. A measuring condition controller variably sets a measuring condition of the color measuring unit in accordance with the patch image to be measured, and a forming condition controller controls an image forming condition on the basis of a measuring result from the color measuring unit.

Another aspect of the invention is a method of color measurement control for forming a color image on a recording material. The method includes forming a plurality of a color image on a recording material, and variably setting a measuring condition to be observed in color-measuring a patch image, in accordance with the patch image to be measured. Each of plural colors of each of a plurality of patch images formed on a recording material is optically measured, by detecting reflected light of each of those colors, from the plurality of patch images. An image forming condition is controlled based on a measuring result obtained in the color measuring step.

Other objects, constructions and effects of the present invention will become apparent from the following detailed description and the accompanying drawings.

BRIEF DESCRIPTION OF THE DRAWINGS

FIG. 4A shows the relation between a patch and predicted reflectance, and FIG. 4B shows the relation between the patch and an amount of irradiating light.

FIG. 5A shows a case where the amount of light of the LED is limited in inverse proportion to the predicted reflectance, and FIG. 5B shows a case where the amount of light of the LED is limited stepwise.

FIG. 8A shows a case where the accumulation time is decreased in inverse proportion to the predicted reflectance, and FIG. 8B shows a case where the accumulation time is decreased stepwise.

FIG. 10A shows a case where the length along the conveyance direction of a patch is decreased in inverse proportion to the predicted reflectance, and FIG. 10B shows a case where the length along the conveyance direction of the patch is decreased stepwise.

FIG. 12 illustrates the memory map of a storage medium storing therein various data processing programs capable of being read out by the image forming apparatus according to the present invention.

FIGS. 13A and 13B illustrate the construction of a color measuring apparatus which can be utilized in an image forming apparatus of this kind.

DESCRIPTION OF THE PREFERRED EMBODIMENTS

First Embodiment

Some embodiments of a color measuring apparatus and a controlling method used in a color image forming apparatus to which the present invention is applied will hereinafter be described in detail with reference to the drawings.

Figure 1:
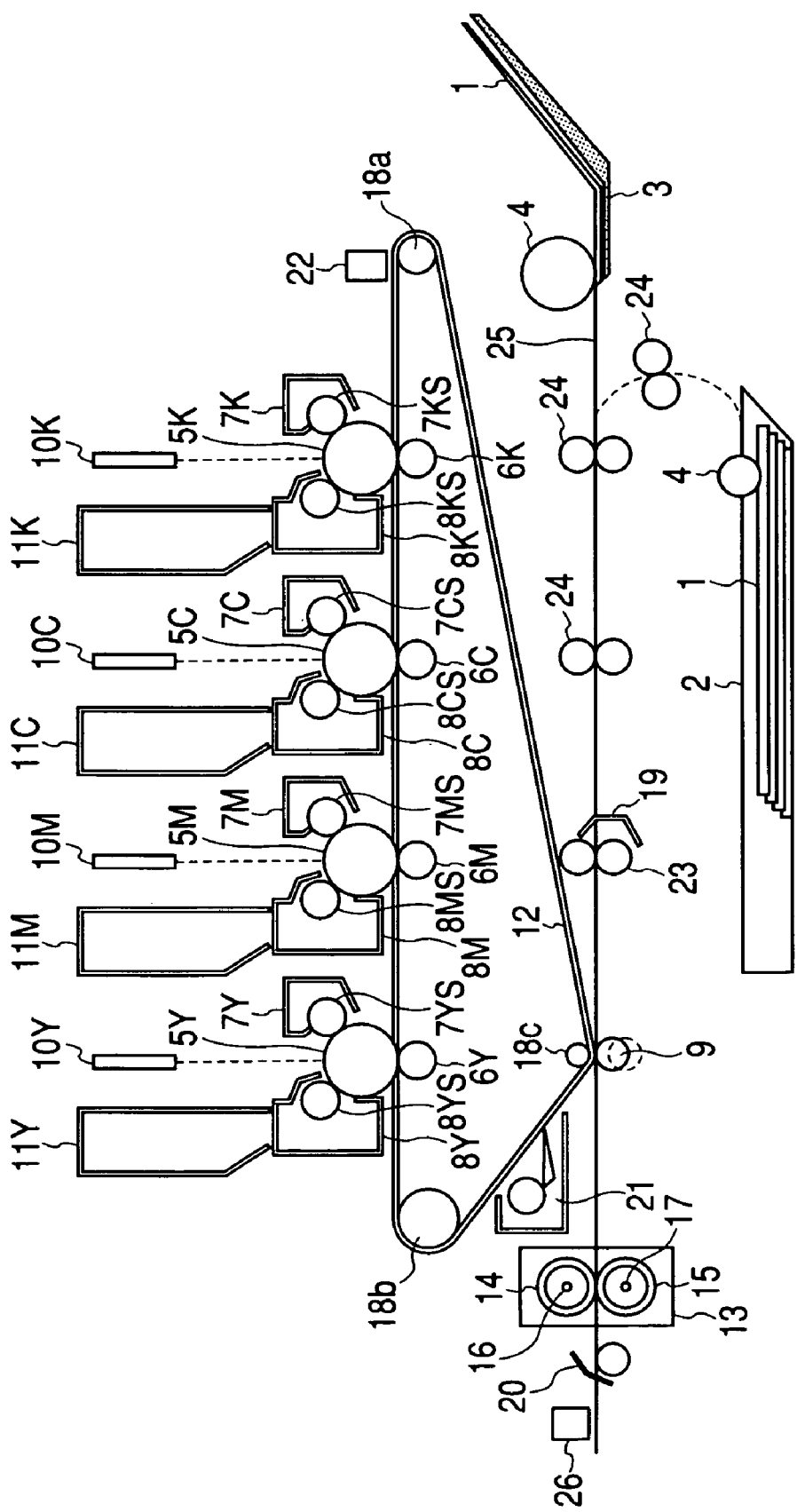
FIG. 1 is a schematic cross-sectional view illustrating the construction of an image forming apparatus according to a first embodiment of the present invention.
Figure 16:
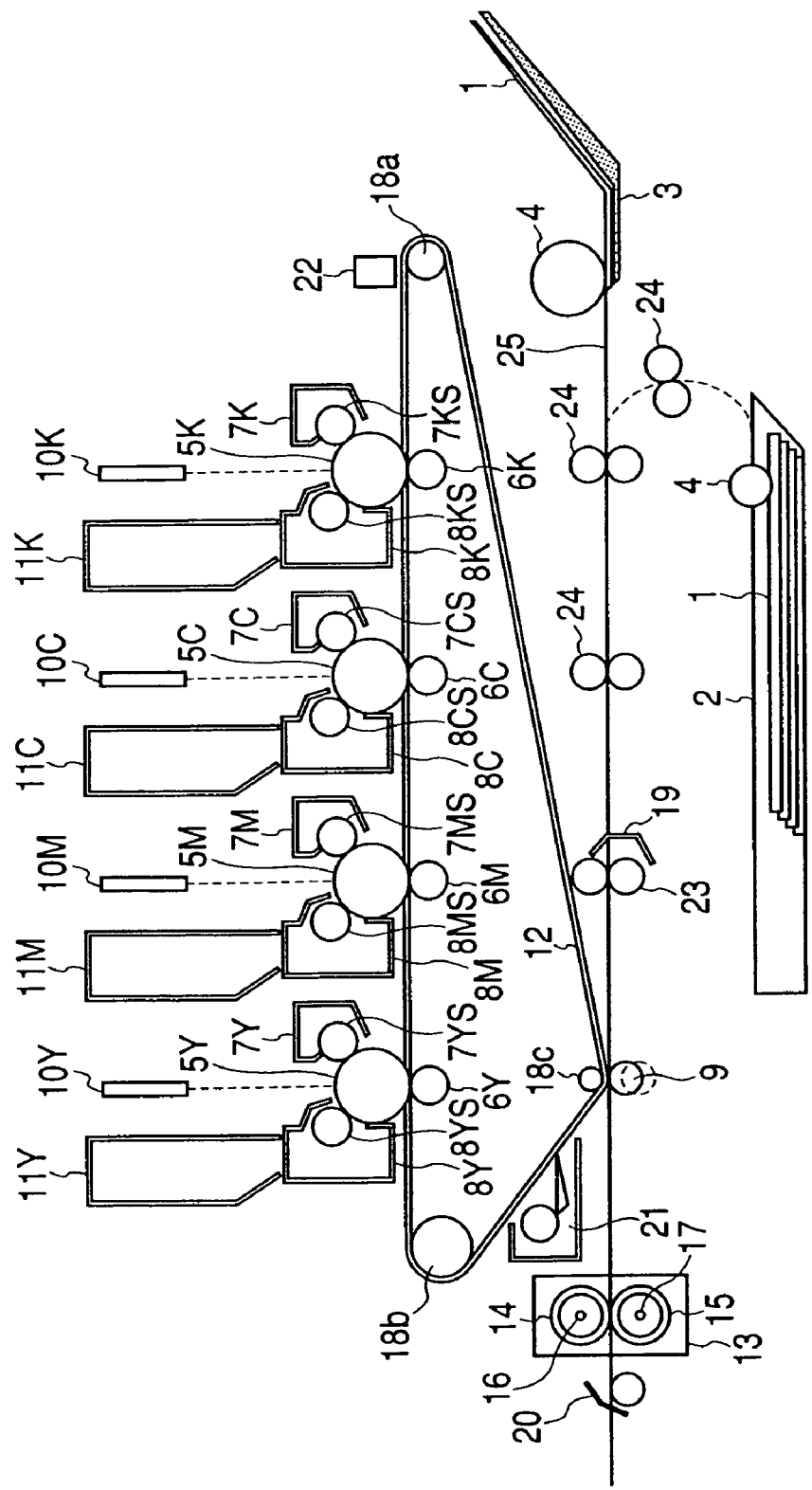
FIG. 16 is a schematic cross-sectional view illustrating the construction of a multicolor image forming apparatus of this kind.

FIG. 1 is a schematic cross-sectional view illustrating the construction of a color image forming apparatus according to a first embodiment of the present invention, and in FIG. 1, the same members as those in FIG. 16 are given the same reference characters.

In FIG. 1, the reference numeral 26 designates a color measuring apparatus which color-measures a patch image formed on a recording medium, at a position underlying the disposed position of a fixing portion B. The color measuring apparatus 26 is designed to be capable of changing a color measuring condition in adaptation to a reflectance predicted from the forming condition of a color image which is an object of detection, in accordance with a control procedure shown, for example, in FIG. 11 on the basis of a control signal from a controller portion, not shown, and detecting an amount of reflected light, and adjusting the image forming condition from the amount of reflected light of the detected single-color or mixed-color image, thereby to effect accurate color measurement of the image of each color, and accurate detection of the hue and density of the color image which is the object of detection, and to form a color image excellent in color reproducibility.

In the present embodiment, the color measuring apparatus 26 is used as a sensor for detecting the colors of toners on paper after fixing and therefore is disposed at a location intermediate between the fixing portion 13 of FIG. 1 and a sheet discharging port (not shown).

In this image forming apparatus, control can be effected so as to apply feedback to a process condition such as a developing bias and gradation correcting means such as a look-up table from the output of each of R, G and B sensors having read reflected light from a toner patch fixed on a transferring material 1, thereby to produce a desired hue on the transferring material.

Even if at this time, the reflectance of the toner patch is low, the amount of light emitted by the LED can be increased, thereby to take out an accurate signal with the signal not obscured by noise, and therefore, control of the image forming condition based on information of high accuracy becomes possible, and an improvement in the accuracy of color stabilization control can be achieved. The other operations of the image forming apparatus are the same as those of the example of the prior art and therefore need not be described.

Figure 2:
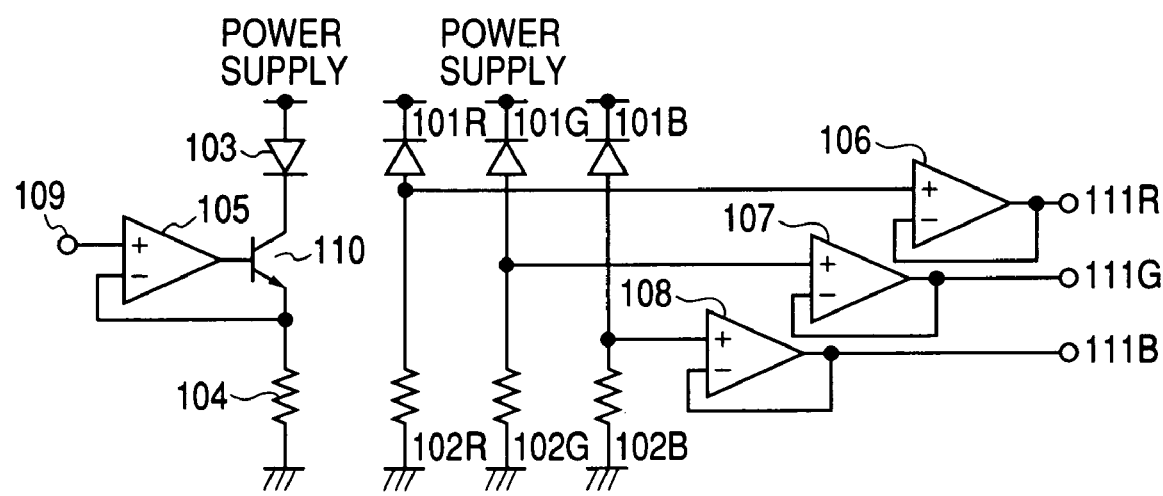
FIG. 2 is a circuit diagram showing an example of the detection circuit of a color measuring apparatus shown in FIG. 1.

FIG. 2 is a circuit diagram showing an example of the detection circuit of the color measuring apparatus 26 shown in FIG. 1.

In FIG. 2, a light receiving portion is comprised of photodiodes 101R, 101G and 101B provided with R, G and B color filters, respectively. Photocurrents generated by the photodiodes 101R, 101G and 101B are converted into voltage signals by resistors 102R, 102G and 102B, and become output signals 111R, 111G and 111B impedance-converted by buffers 106, 107 and 108 constituted by operational amplifiers.

On the other hand, an illuminating system is constituted by a white LED 103 having a light emission spectrum in an entire visible light area, and a driving current control circuit for the LED comprising an operational amplifier 105, a resistor 104 and an NPN transistor 110. A voltage signal 109 for controlling an electric current flowing to the white LED 103 is supplied from a DA converter, not shown.

Feedback is applied to the operational amplifier 105 so that the voltage signal 109 inputted to the non-reversal input terminal of the operational amplifier 105 may be generated on the anode side of the resistor 104. Accordingly, an electric current determined by the voltage signal 109 and the resistance value of the resistor 104 flows to the emitter of the NPN transistor 110, and substantially the same collector current becomes a driving current for the white LED 103. Accordingly, by controlling the voltage level of the voltage signal 109, the driving current for the white LED 103 can be adjusted to thereby adjust the amount of emitted light.

Figure 3:
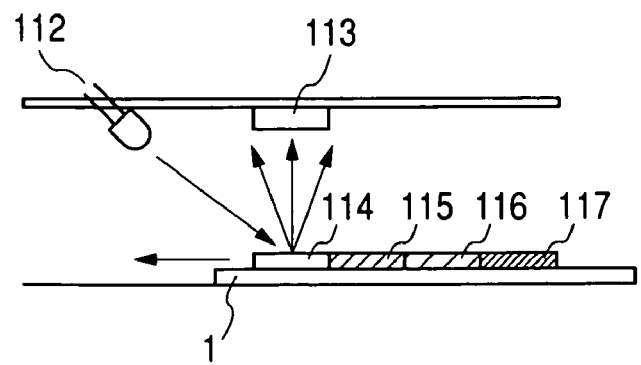
FIG. 3 illustrates the color measuring operation of the color measuring apparatus shown in FIG. 1.

FIG. 3 illustrates the color measuring operation of the color measuring apparatus 26 shown in FIG. 1. In FIG. 3, the reference numeral 112 designates the illuminating system, and the reference numeral 113 denotes the light receiving portion constituted by the three photodiodes. A patch of a single color C, M, Y or K or a mixture of these colors is formed from the heads of the directions of arrows in FIG. 3. As shown in FIG. 3, the transferring material 1 to which respective developers are transferred is conveyed in the direction of arrow (leftward) in FIG. 3, and toner patches 114 to 117 are formed on the transferring material 1. The reflectance of the toner patch 114 on the transferring material 1 is greatest, and the reflectance becomes gradually smaller and the reflectance of the toner patch 117 becomes smallest.

Figure 4A:
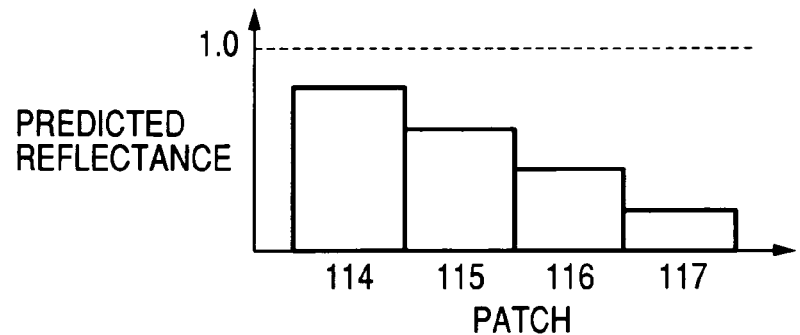
FIGS. 4A and 4B are characteristic graphs illustrating the detecting operation of the color measuring apparatus shown in FIG. 2.
Figure 4B:
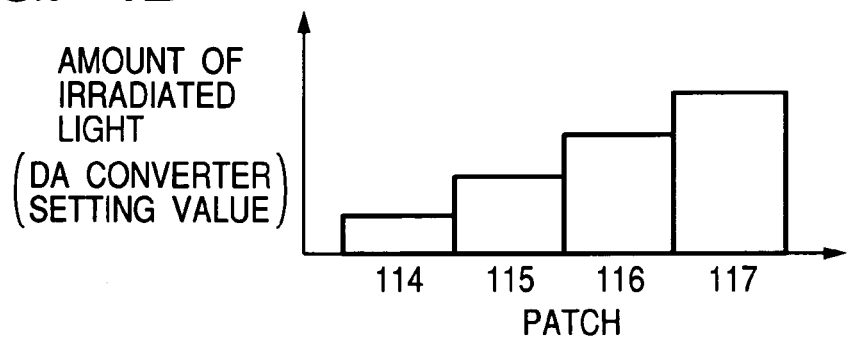

FIGS. 4A and 4B are characteristic graphs illustrating the detecting operation of the color measuring apparatus shown in FIG. 1. FIG. 4A shows a predicted reflectance (foreseen reflectance) detected when the patches 114 to 117 shown in FIG. 3 are irradiated with a constant amount of light, along the directions of the axis of abscissas and the axis of ordinates of FIG. 4A. FIG. 4B shows the adjusted state of the amount of light of FIG. 4A to the patches 114 to 117, and the axis of ordinates of FIG. 4B indicates the amount of irradiating light, and the direction of the axis of abscissas indicates the respective patches 114 to 117.

For the color stabilization control of the color image forming apparatus, it is more desirable to detect more patches and feed back the result to the image forming condition, but here, for simplicity, a case where four patches are read will be described.

The light receiving portion 113 receives reflected lights from the toner patches 114 to 117 one after another, and outputs R, G and B signals 111R, 111G and 111B corresponding thereto.

The reflectance predicted from the image forming condition such as the amounts of side of C, M, Y and K toners in this case becomes gradually smaller as shown in FIG. 4A. In contrast, as shown in FIG. 4B, an input voltage applied to the illuminating system 112 can be changed in conformity with predicted reflectance to thereby adjust an LED driving current, i.e., the amount of light, and control so that the output may be substantially constant.

When this control is not effected, the output 111 becomes small for a patch of low reflectance like the toner patch 117 corresponding to black, and the signal is buried in a quantization error when AD conversion is done or the noise of a reading-out circuit, and the R, G and B components of correct reflected light cannot be obtained.

Also, when as shown in FIG. 4B, the amount of light is increased in accordance with a toner patch of low reflectance like black, the sensor output is saturated with the patch 114 of, e.g., Y, a color which is high in reflectance, and again in this case, correct color measurement becomes impossible.

On the other hand, by this control being put in, in the case of a patch which is predicted to be low in reflectance from the image forming condition, the amount of light from the illuminating system 112 is increased, and the read-out signal level will not be low, and is very unlikely to be affected by the quantization error or by noise of the reading-out system, and thus the R, G and B components of the reflected light can more accurately be obtained.

The R, G and B signals after AD-conversion are converted into the values of the same amount of light condition (as an example, the amount of light of the LED is substantially proportional to the driving current and therefore can be multiplied by a value corresponding to the inverse number of the value of a DA converter set during measurement), the chromaticity of the corresponding toner patch is calculated, and the image forming condition is changed so as to correct the deviation from desired chromaticity.

What patch is formed and what feedback is applied to the image forming apparatus are as proposed in Japanese Patent Applications Laid-Open Nos. 2001-273508 and 2001-297068 of the assignee of the present invention.

Figure 5A:
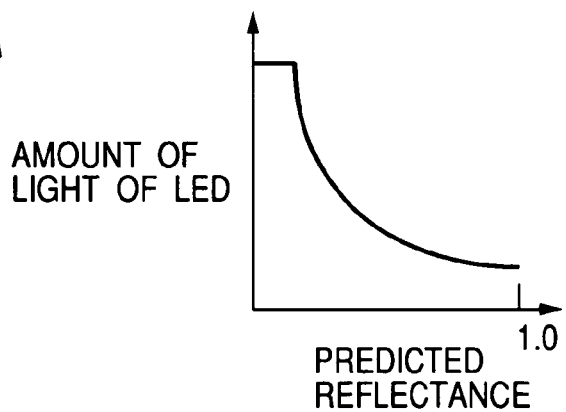
FIGS. 5A and 5B are graphs showing the relation between the predicted reflectance and the manner of changing the amount of light of an LED.
Figure 5B:
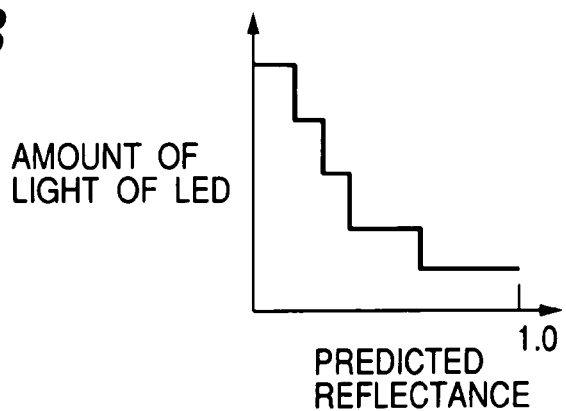

Also, as regards the manner of changing the amount of light for the predicted reflectance, it is basic to make the amount of light great for the lower reflectance, and as shown in FIG. 5A, the amount of light may be continuously changed in inverse proportion to the predicted reflectance (within such a range as will not exceed the upper limit of the allowable amount of light of the LED); as another approach, as shown in FIG. 5B, stepwise control such that a constant amount of light is set within a certain range of reflectance and if the range is exceeded, a new amount of light is set, may be used.

The sensor used is not restricted to a photodiode, but of course may be a sensor like a phototransistor which generates an output current conforming to an incident light, or an accumulation type sensor like a CCD or a CMOS sensor which accumulates a photocurrent therein for a predetermined time, and thereafter converts it into a voltage and outputs it.

Also, while an example of the sensor provided with color filters on a white light source has been shown herein, of course it is also possible to use three light sources of different spectra and a sensor provided with no color filter to turn on three or more light sources one after another with respect to a toner patch and obtain sensor outputs corresponding to the respective light sources.

The reflectance of each of the R, G and B components is varied by the hue of the patch, and therefore, there is a patch of a hue which is great in the reflectance of the entire visible light but is small in the reflectances corresponding to the spectrum of the individual light sources. In this case, electric currents flowing to a plurality of light sources are changed for a toner patch to control the output so as to be substantially constant.

As described above, according to the image forming apparatus in the first embodiment, during the detection of the chromaticity of the toner patch formed by the color image forming apparatus, the amount of light of the light source is changed in conformity with the predicted reflectance of the toner patch by a circuit which will be described later, so that the output is not saturated even for a toner patch of great reflectance (e.g., the Y patch), and the influence of the quantization error or the noise of the reading-out circuit during AD conversion can be reduced even for a patch of small reflectance (e.g., the K patch) and chromaticity information of high accuracy can be obtained.

Further, by providing feed-back to the color image forming apparatus by the use of the obtained information, it is possible to achieve an improvement in color stability.

Second Embodiment

In the first embodiment, description has been made of a case where the amount of light of the white LED 103 in the color measuring apparatus 26 is varied and controlled to adjust the sensor outputs 111R, 111G and 111B, but when the amount of emitted light is controlled with the driving current for the LED 103 greatly changed, there is the problem that the rate of light emission changes over several seconds, and when the patches on the transferring material being conveyed are to be detected, there has been the problem that the detection interval between the patches increases and the number of patches which can be detected in the limited size of the transferring material decreases.

So, in the present embodiment, there is proposed a color measuring apparatus which increases the accuracy of color measurement without varying the light output of the white LED 103.

For this purpose, in the present embodiment, a sensor of the accumulation type typified, for example, by a CMOS sensor is used as the light receiving portion 113 of the color measuring apparatus shown in FIG. 3. As the white LED 103 of the illuminating system, use is made of a white LED having a spectrum in the entire visible light area as in the first embodiment and therefore, this need not be described in detail.

Figure 6:
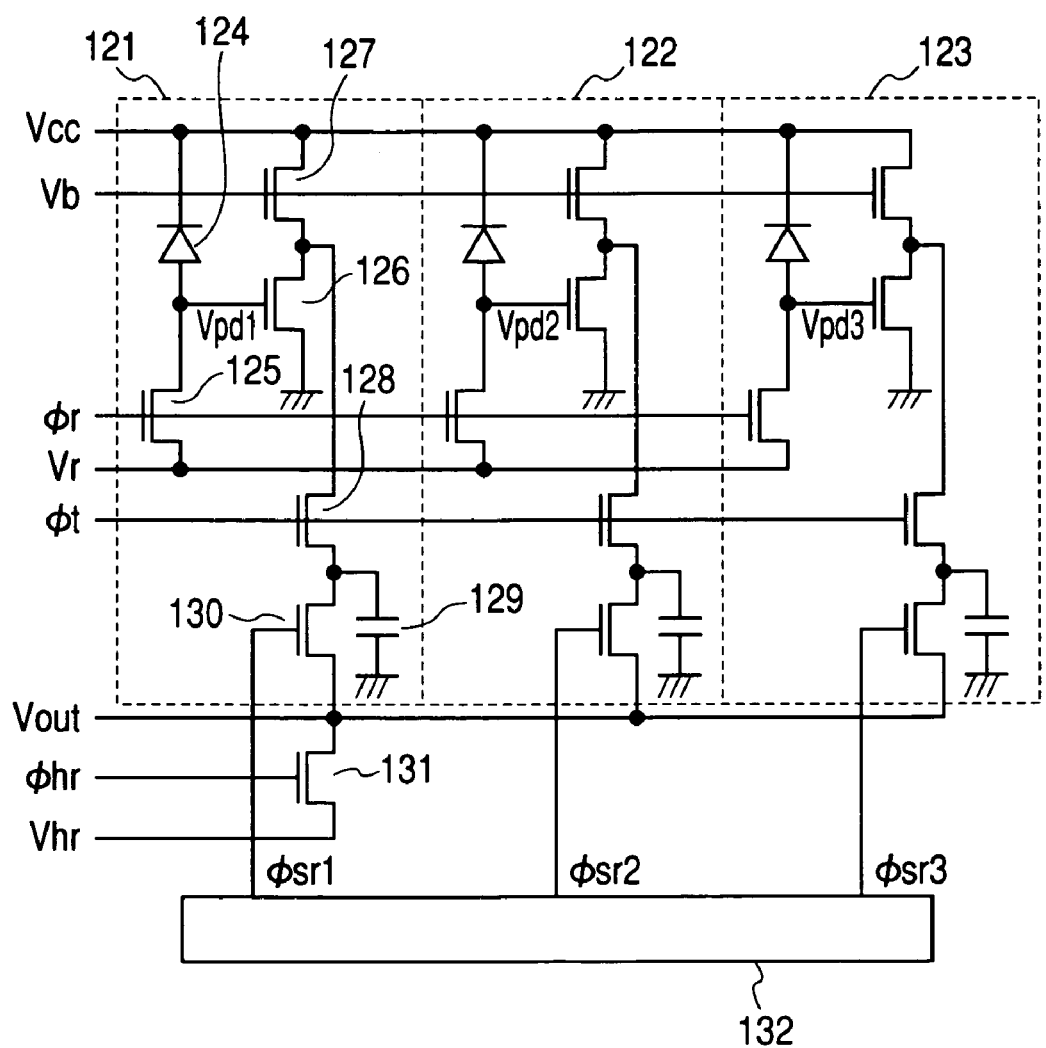
FIG. 6 illustrates the construction of a circuit in the color measuring apparatus of an image forming apparatus according to a second embodiment of the present invention.

FIG. 6 illustrates the construction of a circuit in the color measuring apparatus of a color image forming apparatus according to a second embodiment of the present invention, and in the present embodiment, an accumulation type sensor of a CMOS type is used as a sensor element.

Figure 7:
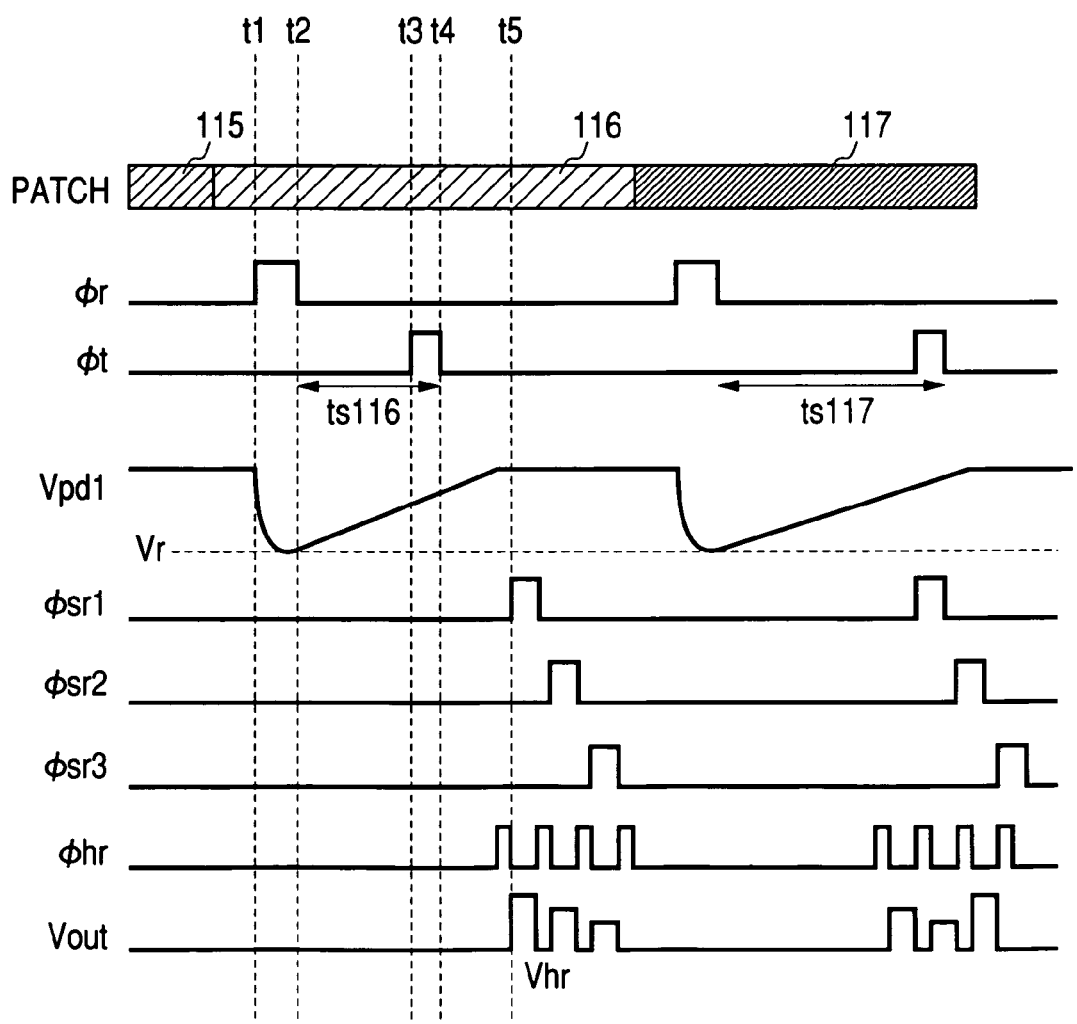
FIG. 7 is a timing chart illustrating the operation of a CMOS sensor shown in FIG. 6.

FIG. 7 is a timing chart illustrating the operation of the CMOS sensor shown in FIG. 6. Description will hereinafter be made of the operation of a pixel of the CMOS sensor. In FIG. 6, the reference numeral 124 designates a photodiode for detecting light. The reference numeral 125 denotes NMOSFET for resetting the photodiode to reset potential Vr on the basis of a sensor reset signal φr, and the reference numeral 126 designates a PMOSFET for outputting the anode potential Vpd of the photodiode 124 by a source follower.

The reference numeral 127 denotes a PMOSFET to the gate of which a constant voltage Vb is applied and which supplies a constant current to the source follower. The reference numeral 128 designates an NMOSFET for collectively forwarding the outputs of respective sensors to a capacitor 129 on the basis of a forwarding signal φt.

The reference numeral 130 denotes an NMOSFET for outputting the charges forwarded to the capacitor 129 to an output line Vout in conformity with the output φsr1 of a shift register 132. The reference numeral 131 designates an NMOSFET for resetting the output line Vout to a voltage Vhr on the basis of an output line reset signal φhr.

In the present embodiment, the sensor shown in FIG. 6 is provided for three pixels (pixels 121, 122, 123) correspondingly to R, G and B colors, and R, G and B on-chip color filters are provided on the surfaces of the respective pixels, whereby it becomes possible to detect signals of three colors, i.e., R, G and B, of reflected light.

The signal outputted to the output line Vout is buffered by an operational amplifier or the like, and thereafter is AD-converted, whereby it is possible to obtain a signal resulting from lights corresponding to the wavelengths of R, G and B components of reflected light reflected by the surface of the toner having been accumulated for a predetermined time.

Each driving signal is supplied from a CPU or the like (not shown) for controlling the operation of the color image forming apparatus.

The operation of the CMOS sensor in the present embodiment will hereinafter be described with reference to the timing chart of FIG. 7.

Here, description will be made of the patch detecting operation for patches 116 and 117 of small predicted reflectance among the four toner patches shown in the first embodiment.

First, by the image forming apparatus shown in FIG. 1, patches to be detected are formed on the transferring material 1 in each image station on the basis of stored patch image data.

The white LED 103 of the illuminating system shown in FIG. 3 is continuously made to emit light by a constant electric current throughout detection.

At this time, the sensor reset signal φr assumes a high state (H) at a time t1, and the NMOSFET 125 is turned on and the anode of the photodiode is reset to the voltage Vr. At a time t2, the sensor reset signal φr assumes a low state (L), and when the reset of the photodiode 124 is released, the accumulation by the sensor is started.

The timing of time t2 is set to a state in which the toner patch on the transferring material has sufficiently entered the detection range of the sensor, in order to avoid color mixing with an adjacent toner patch during color measurement.

During accumulation, the anode potential Vpd1 of the photodiode 124 rises by the photocurrent by the R component of the incident light. Likewise, the anode potentials Vpd2 and Vpd3 of the photodiodes of pixels 122 and 123 rise in conformity with the intensity of the G component and B component of the incident light.

After the lapse of a predetermined accumulation time, at a time t3, the forwarding signal φt is brought into a high state (H), whereupon the NMOSFET 128 is turned on, and an output voltage resulting from the anode potential Vpd1, buffered by a source follower circuit, is forwarded to the capacitor 129.

At a time t4, the forwarding signal φt assumes a low state (L), thereby terminating the forwarding to the capacitor 129. This interval becomes an accumulation time (ts) 116. The pixels 122 and 123 operate in the same way.

Thereafter, the shift register 132 is operated to bring a shift pulse φsr1 into a high state (H), and the NMOSFET 130 is turned on to read out an output pulse Vout, which is the output of the sensor.

The output pulse Vout thus read out is AD-converted by an AD converter (not shown) and is contained in the memory of a CPU (not shown) which controls the operation of the image forming apparatus.

After the output of a sensor has been read out, the output line brings the pulse φhr into a high state (H), whereby it is reset to a reset pulse Vhr by the NMOSFET 131. The shift register turns on shift pulses φsr2 and φsr3 one after another and reads out sensor outputs corresponding to the subsequent G and B filters.

After a signal corresponding to the toner patch 116 has been read out, the detection of the toner patch 117 is likewise effected.

It is a characteristic of the present embodiment that the accumulation time (ts117) in this case is increased or decreased in conformity with the reflectance predicted from the image forming condition. In this embodiment, as compared with the toner patch 116, the density of the toner patch 117 is high and the reflectance predicted from the image forming condition is low, and therefore, the accumulation time ts117 corresponding to the toner patch 117 is made longer than ts116, and with respect also to the patch of low reflectance, the output of the sensor is made great as compared with the quantization error during AD conversion or the noise level of the reading-out system. Although not shown, in the case of a toner patch conversely having great predicted reflectance, the accumulation time is made short, to prevent the saturation of the sensor.

When the present color measuring apparatus is carried on the color image forming apparatus to effect the stabilization of the quality of image, R, G and B signals corresponding to a plurality of toner patches after AD-converted are converted into the values under the condition of the same accumulation time (as an example, they may be multiplied by a value corresponding to the inverse number of the accumulation type during measurement), the chromaticity of the corresponding toner patch is calculated, and feedback is applied to several kinds of exposure amounts conforming to the absolute humidity corresponding to the toner of each color, the process condition such as the developing bias, and the gradation correcting means such as the look-up table to thereby control so as to provide a desired hue on the transferring material, but this is similar to the case of the first embodiment and therefore need not be described.

Figure 8A:
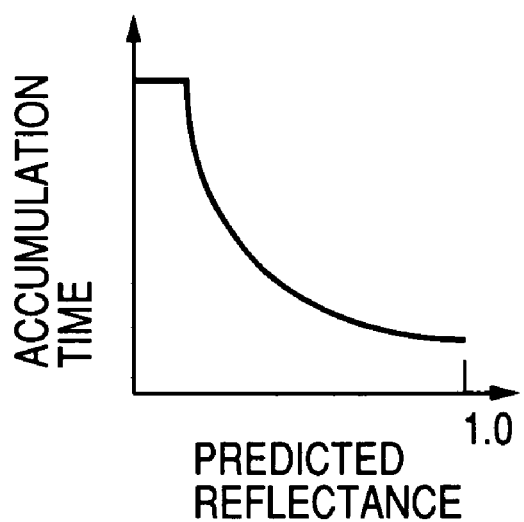
FIGS. 8A and 8B are characteristic graphs illustrating the correspondence of an accumulation time and a predicted reflectance to a capacitor shown in FIG. 6.
Figure 8B:
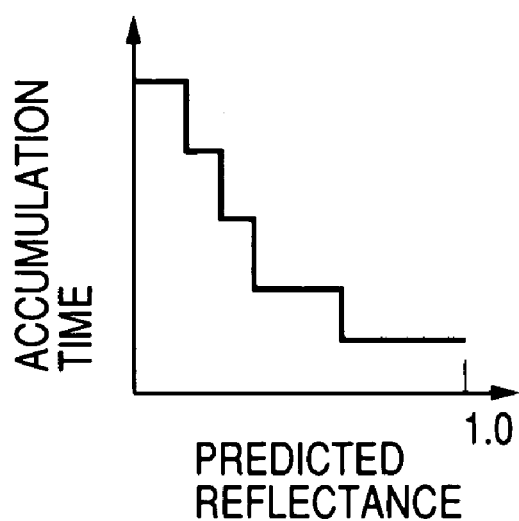

FIGS. 8A and 8B are characteristic graphs illustrating the correspondence of the accumulation time and the predicted reflectance to the capacitor 129 shown in FIG. 6. FIG. 8A corresponds to a case where the accumulation time is continuously changed so as to be inversely proportional to the predicted reflectance FIGS. 8A and 8B show an example in which in the case of a reflectance within a certain range. The accumulation time is changed stepwise so as to be constant. In FIGS. 8A and 8B, the axis of ordinates indicates the accumulation time, and the axis of abscissas indicates the predicted reflectance.

Also, the relation between the predicted reflectance of the toner patches and the accumulation time is such that it is basic to make the accumulation time long for the toner patch of smaller reflectance, but as shown in FIG. 8A. The accumulation time may be continuously changed so as to be inversely proportional to the predicted reflectance, or as shown in FIG. 8B, in the case of a reflectance within a certain range, the accumulation time may be changed stepwise so as to be constant.

As described above, the accumulation type sensor is used and the accumulation time thereof is changed in conformity with the reflectance predicted from the image forming condition of the toner patches, whereby, without the adjustment of the amount of light of the LED for each toner patch, the influence of the quantization error during AD conversion or the noise of the reading-out circuit can be reduced even for a toner patch of small reflectance, and color information of high accuracy can be obtained. Further, an improvement in the color stability of the color image forming apparatus can be realized by the use of the obtained information.

Herein, the example of three sensors carrying three R, G and B filters thereon has been shown as the sensor for detecting the chromaticity of the toners.

However, the number of the sensors is not limited to three, but of course, in order to make symmetry good, a plurality of dummy pixels may be provided on both sides, or a plurality of pixels corresponding to R, G and B filters may be provided, and such control as takes the sum or average of the outputs thereof and averages the positional unevenness of the toner patches to thereby improve accuracy may be effected. Also, the wavelengths transmitted through the filters are not limited to R, G and B.

Further, of course, there is also a similar effect in a case where a line sensor provided with a number of sensors designed such that reflected light from a toner patch is separated by a prism or a diffraction grating and lights of different wavelength ranges enter respective pixels, or light sources of different light emission wavelengths such as R, G and B LEDs are changed over to thereby measure the reflected light of the toner patch by a sensor.

Also, herein, the example of the CMOS sensor has been shown as the accumulation type sensor. Of course, however, the kind of the sensor is not particularly restricted, but use may be made of any accumulation type sensor such as CCD or BASIS.

Third Embodiment

In the above-described second embodiment, description has been made of a case where the length of each toner patch is made constant and the accumulation time is varied by the predicted reflectance, but in a case where the maximum value of the accumulation time is determined in accordance with the toner patch of the detected lowest reflectance and the lengths of all toner patches are set to the length of the toner patch corresponding thereto, the number of patches which can be formed on the limited length of the transferring material decreases and the comparison between the actual chromaticity of various patches and the desired chromaticity becomes impossible. As a result, the color stabilization of the color image forming apparatus must be contrived on the basis of the result of the detection of few patches, and this leads to a disadvantage in accuracy.

It is also conceivable to make such design that measurement is effected with the transferring material stopped during each measurement so as not to decrease the number of patches, but this is undesirable for the following reasons. That is, control becomes complicated, the time required for color measurement lengthens and the throughput falls, the transferring material cannot be stopped until it passes through the fixing device and the location at which the color measuring apparatus can be disposed is limited, etc.

So, in the present embodiment, not only is the accumulation time of the accumulation type sensor changed in conformity with the reflectance predicted from the forming condition of the toner patches, but the lengths of the toner patches in the conveyance direction are made variable.

The construction of the sensors used in the color measuring apparatus shown in FIG. 2 is the same as that in the second embodiment and therefore need not be described.

Figure 9:
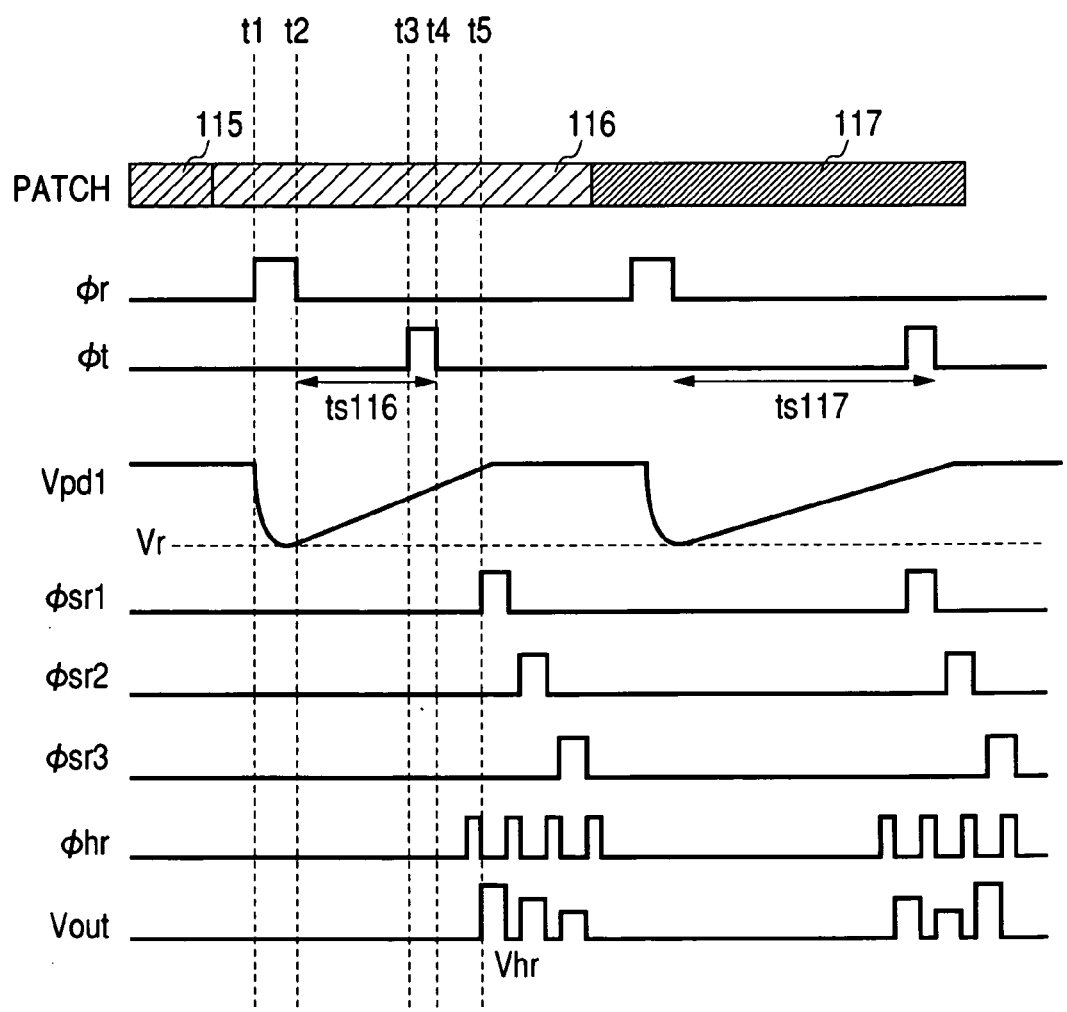
FIG. 9 is a timing chart illustrating the operation of the CMOS sensor shown in FIG. 6.

FIG. 9 is a timing chart illustrating the operation of the CMOS sensor shown in FIG. 6, and in FIG. 9, the same reference characters are those in FIG. 7 are the same in significance. This example of the operation will also be described with respect to the patches 116 and 117 of the toners of relatively low reflectance as in the second embodiment.

First, toner patches having their lengths changed in conformity with the reflectance predicted from the forming condition of the respective patches are formed on the transferring material 1. The white LED 103 of the illuminating system shown in FIG. 3 is continuously made to emit light by a constant electric current throughout patch detection.

At the time t1, the reset signal φr assumes a high state (H), the NMOSFET 125 is turned on and the anode of the photodiode is reset to a voltage Vr. At the time t2, the reset signal φr assumes a low state (L), and when the reset of the photodiode 124 is released, accumulation is started.

During the accumulation, the potential Vpd1 of the anode of the photodiode 124 rises by a photocurrent. Likewise the potentials Vpd2 and Vpd3 of the anodes of the photodiodes of the pixels 122 and 123 rise in conformity with the intensity of the incident light.

When after the lapse of a predetermined time, at the time t3, φt assumes a high state, the NMOSFET 128 is turned on, and an output voltage resulting from Vpd1 having been buffered by the source follower circuit is forwarded to the capacitor 129.

At the time t4, φt is brought into a low state (L), thus terminating the forwarding to the capacitor 129. This time is an accumulation time t2 116. Thereafter, the shift register 132 is operated, and at the time t5, φsr1 is brought into a high state (H), the NMOSFET 130 is turned on, and the output of the sensor is read out at Vout.

The signal thus read out is AD-converted by an AD converter (not shown) and is contained in the memory of a CPU (not shown) for controlling the operation of the image forming apparatus. After the output of a sensor has been read out, the output line brings φhr into a high state (H), whereby it is reset to Vhr by the NMOSFET 121. Next, the shift register turns on φsr2 and φsr3 one after another, and reads out sensor outputs corresponding to the subsequent G and B color filters.

After a signal corresponding to the first toner patch 116 has been read out, the detection of the toner patch 117 is likewise effected. As compared with the toner patch 116, the density of the toner patch 117 is high and the reflectance predicted from the image forming condition is low, and therefore, the accumulation time ts117 corresponding to the toner patch 117 is made longer than ts116, and with respect also to the patches of low reflectance, the output of the sensor is made great as compared with the quantization error during AD conversion or the noise level of the reading-out system, as in the second embodiment.

In the present embodiment, further, the lengths of the patches along the conveyance direction are changed in conformity with the predicted reflectance. The length of the toner patch 117 of relatively low reflectance along the conveyance direction is lengthened and therefore, even if the accumulation time is lengthened, the detection range of the sensor does not extend to the next patch and detection can be effected. Conversely, in the case of a patch of great predicted reflectance, the length of the patch along the conveyance direction and the accumulation time can be made short, and the limited length of the transferring material can be efficiently used and color measurement of high accuracy becomes possible without the number of detectable patches being decreased.

In a case where the color measuring apparatus shown in FIG. 6 is carried on the image forming apparatus to effect the stabilization of the quality of image, R, G and B signals corresponding to a plurality of toner patches after AD-converted are converted into the value of the condition of the same accumulation time (as an example, they can be multiplied by a value corresponding to the inverse number of the accumulation time during measurement), chromaticity of the corresponding toner patch is calculated, and feedback is applied to the process condition such as the developing bias and the gradation correcting means such as a look-up table so as to provide a desired hue on the transferring material, but this is similar to the case of the first embodiment and therefore need not be described.

Also, as in the second embodiment, the relation between the predicted reflectance of the toner patch and the accumulation time is such that it is basic to make the accumulation time longer for the patch of smaller reflectance, but as shown in FIG. 8A, the accumulation time may be continuously changed so as to be inversely proportional to the predicted reflectance, or as shown in FIG. 8B, in the case of a certain range of reflectance, the accumulation time may be changed so as to be made constant.

Figure 10A:
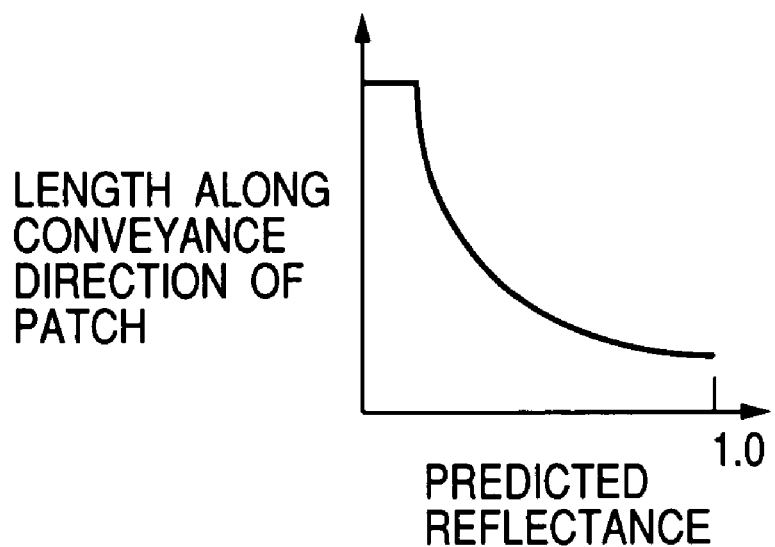
FIGS. 10A and 10B are characteristic graphs illustrating the detecting operation of the color measuring apparatus shown in FIG. 6.
Figure 10B:
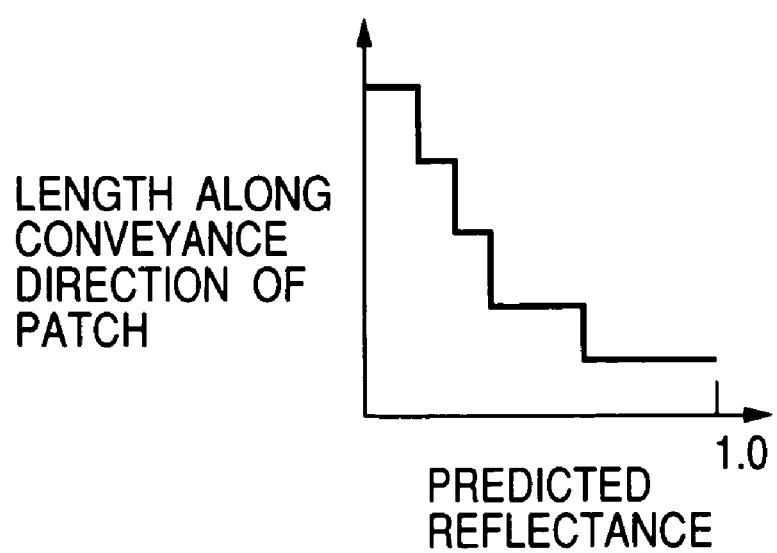

As regards the manner of changing the length of the patch in the conveyance direction conforming to the predicted reflectance of the toner patch, it is basic to make the patch of smaller reflectance longer, but as shown in FIG. 10A, the length of the patch may be continuously changed so as to be inversely proportional to the predicted reflectance, or as shown in FIG. 10B, in the case of a certain range of reflectance, the length of the patch may be changed stepwise so as to be made constant.

As described above, the accumulation type sensor is used and the accumulation time thereof is changed in conformity with the reflectance predicted from the image forming condition of the toner patch, whereby without the adjustment of the amount of light of the LED for each toner patch, the influence of the quantization error during AD conversion or the noise of the reading-out circuit can be reduced even for a toner patch of small reflectance, and color information of high accuracy can be obtained.

Also, the length of the patch can be changed in conformity with the predicted reflectance thereof, whereby the limited length of the transferring material can be effectively used to thereby realize the color measurement of high accuracy, and by the use of information obtained therefrom, an improvement in the color stability of the color image forming apparatus can be realized.

Herein, the example of three sensors having three R, G and B filters put thereon has been shown as the sensor for detecting the chromaticity of the toner. However, the number of sensors is not restricted to three, but in order to make symmetry good, of course, such control as provides a plurality of dummy pixels on both sides or provides a plurality of pixels corresponding to the R, G and B filters, and takes the sum or average of the outputs thereof and averages the positional unevenness of the toner patches to thereby improve accuracy may be effected. Also, the wavelengths transmitted through the filters are not limited to R, G and B.

Further, of course, there is also a similar effect in a case where a line sensor provided with a number of sensors designed such that correspondingly to a spectral photometry method, lights of different wavelength ranges enter them, or light sources of different light emission wavelengths such as R, G and B LEDS are changed over to thereby measure the reflected lights of the toner patches by a sensor. Also, herein, the example of a CMOS sensor has been shown as the accumulation type sensor. Of course, however, the kind of the sensor is not particularly restrictive, but use may be made of any accumulation type sensor such as CCD or BASIS.

Fourth Embodiment

In the first embodiment to the third embodiment, reflectance is predicted from the forming condition of the toner patch, and the amount of light and the accumulation time are controlled. This method is premised on the idea that image forming is effected normally, and when the image forming condition remarkably deviates from a normal state, there is the possibility that the sensor output is saturated (when the reflectance deviates toward an extremely great side) or conversely the signal level becomes extremely small.

So, in the present embodiment, design may be made such that the color measuring apparatus controls the amount of light and the accumulation time on the basis of not only the reflectance predicted from the forming condition of the toner patch but also the actually measured reflectance by the CPU executing a measurement control program stored in a ROM provided on a controller substrate, not shown, so that accurate color measurement may be made possible even when the image forming condition remarkably deviates from the normal state. This embodiment will hereinafter be described. The construction of the image forming apparatus corresponds to that of the color image forming apparatus shown in FIG. 1.

Figure 11:
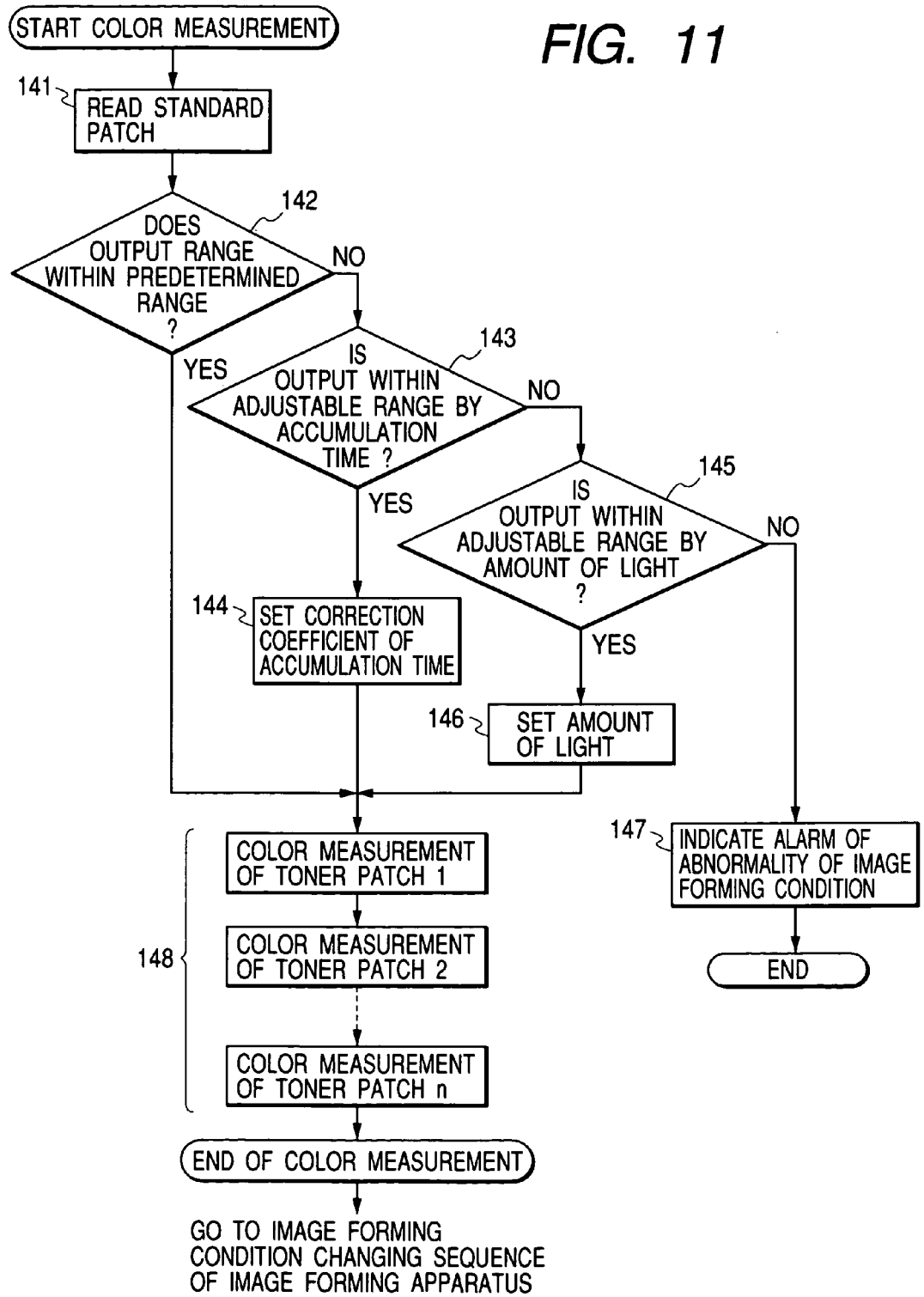
FIG. 11 is a flow chart showing an example of the color measuring process procedure in an image forming apparatus according to the present invention.
Figure 14:
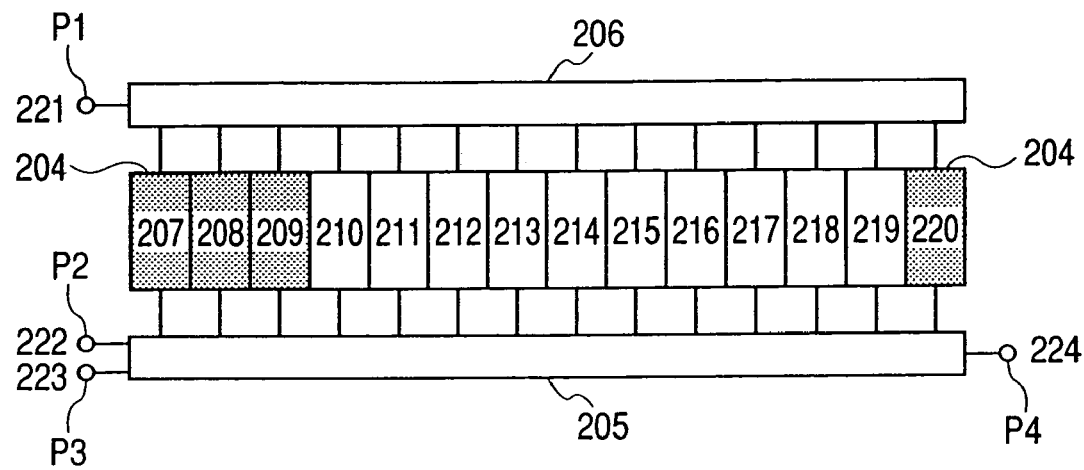
FIG. 14 is a block diagram showing the pixel construction of a line sensor of an accumulation type utilized in a conventional image forming apparatus.
Figure 15:
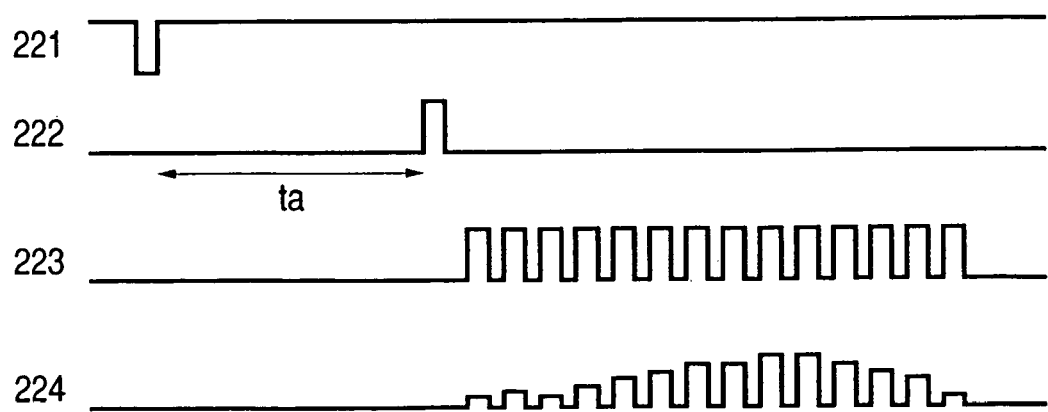
FIG. 15 is a timing chart illustrating the operation timing of the line sensor of the accumulation type shown in FIG. 14.

FIG. 11 is a flow chart showing an example of the color measuring process procedure in the color image forming apparatus according to the present invention. Numbers (141) to (148) designate steps.

First, the color measurement of a standard patch of a mixture of C, M, Y and K (141), and the magnitudes of the signal levels are judged (142), and if it is judged that the signal levels of the sensors of the color measuring apparatus are normal, the detection of the toner patches is effected by the method shown in the color measuring process of one of the first embodiment to the third embodiment (148).

On the other hand, if at the step (142), it is judged that the signal levels of the sensors of the color measuring apparatus are not normal, at a step 143, whether the signal levels are not normal, but yet are not extremely great or small and are correctable by the adjustment of the accumulation time is judged, and if it is judged that they are correctable by the adjustment of the accumulation time, at a step (144), an accumulation time correction coefficient is set, and advance is made to a step (148).

The accumulation time correction coefficient is a coefficient to multiply the accumulation times of all toner patches when the accumulation time adjustment as shown in the second embodiment and the third embodiment is effected to thereby detect the reflected light from the toner patches, and a case where there is particularly no abnormality in the image forming condition, but a predetermined signal level is obtained is "1", and a case where the signal level is too small is a coefficient greater than "1".

Also, the upper limit is such a value that in case of color measurement, the detection area of the sensor does not extend to the next patch. When the signal level is great, the upper limit is a value smaller than 1.

On the other hand, if at the step (143), it is judged that the signal level is not correctable by the adjustment of the accumulation time, at a step (145), that is, if the signal level of the standard patch is outside the range correctable by the adjustment of the accumulation time, whether the signal level is within a range adjustable by the amount of light is judged. The maximum amount of light is determined by the rated current of the LED and therefore, the range adjustable by the amount of light is limited.

If at a step (145), it is judged that the signal level is within the range adjustable by the amount of light, a new amount of light is set (146), and advance is made to the step (148).

On the other hand, if at the step (145), it is judged that the signal level is not within the range adjustable by the amount of light, that is, the signal level is outside such range, at a step (147), the alarm of the abnormality of the image forming condition is put out, thus ending the patch detecting process.

When correction is not necessary, or the signal level is adjustable by the accumulation time and the amount of light, the toner patches 1-n (n being the number of the toner patches) are color-measured, thus ending the measurement. As described above, even when the image forming condition deviates from the normal state, the accumulation time or the amount of light of the light source is adjusted on the basis of the magnitude (the reflectance of the patch) of the signal actually read from the patch, whereby the accurate color measurement of the patch becomes possible.

The construction of a data processing program readable out by the color image forming apparatus according to the present invention will hereinafter be described with reference to a memory map shown in FIG. 12.

FIG. 12 shows the memory map of a storage medium such as a floppy disc or a CD-ROM storing therein various data processing programs readable out by the color image forming apparatus according to the present invention.

Although not particularly shown, there is a case where information for controlling a program group stored in the storage medium, for example, version information, the name of a program maker, etc., is also stored, and information depending on the OS or the like of the program reading side, for example, icon or the like for discriminating and indicating the program is also stored.

Further, data belonging to the various programs are controlled by the above-described directory. There is also a case where a program for installing the various programs in a computer, and a program or the like for thawing the program for installing when it is compressed are also stored.

The function in the present embodiment shown in FIG. 11 may be performed by a host computer by the use of a program installed from the outside. In that case, the present invention is also applied when an information group including the program is supplied to an output apparatus by a storage medium such as a CD-ROM, a flash memory or an FD, or from an external storage medium through a network.

Of course, the object of the present invention is also achieved by supplying a system or an apparatus with the storage medium having recorded therein the program code of software for realizing the function of the aforedescribed embodiments, as described above, and the computer (or the CPU or MPU) of the system or the apparatus reading out and executing the program code stored in the storage medium.

In this case, the program code itself read out of the storage medium realizes the novel function of the present invention and thus, the storage medium storing the program code therein constitutes the present invention.

As the storage medium for supplying the program code, use can be made, for example, of a flexible disc, a hard disc, an optical disc, a magneto-optical disc, a CD-ROM, a CD-R, a magnetic tape, a non-volatile memory card, a ROM, an EEPROM or the like.

Of course, the present invention also covers a case where a program code read out by a computer is executed, whereby not only the function of the aforedescribed embodiments is realized, but also on the basis of the instructions of the program code, an operating system (OS) or the like working on the computer carries out part or the whole of actual processing, and the function of the aforedescribed embodiments is realized by that processing.

Further, of course, the present invention also covers a case where the program code read out of the storage medium is written into a memory provided in a function expanding board inserted into a computer or a function expanding unit connected to the computer, whereafter on the basis of the instructions of the program code, a CPU or the like provided in the function expanding board or the function expanding unit carries out part or the whole of actual processing, and the function of the aforedescribed embodiments is realized by that processing.

The present invention is not restricted to the above-described embodiments, but various modifications (including an organic combination of the embodiments) are possible on the basis of the gist of the present invention, and they are not eliminated from the scope of the present invention.

While various examples and embodiments of the present invention have been shown and described, those skilled in the art would understood that the gist and scope of the present invention are not restricted to the particular descriptions herein.

According to the present invention, the amount of light of the light source of the color measuring apparatus is controlled in conformity with the reflectance predicted from the forming condition of the toner patch and specifically, in a color measuring apparatus for detecting the reflected light from the toner patch on the transferring material to thereby find chromaticity, the amount of light of the light source is changed in conformity with the reflectance of the toner patch, and even for a patch of small reflectance, the signal components are made great and then read and therefore, the influence of the quantization error during AD conversion or the noise of the reading-out circuit can be reduced, and irrespective of the reflectance of the patch, color measurement of high accuracy becomes possible.

Further, the present color measuring apparatus is carried on the color image forming apparatus, and the chromaticity obtained from the toner patch is fed back to the image forming condition, whereby an image of a stable hue can be obtained.

As described above, the amount of light of the light source is controlled, whereby even toner patch of low reflectance can be read out at a great signal level and detection good in S/N and reduced in the influence of the quantization error or the noise of the circuit can be accomplished.

Also, the accumulation time of the accumulation type sensor of the color measuring apparatus is controlled in conformity with the reflectance predicted from the forming condition of the toner patch and specifically, in a color measuring apparatus for detecting the reflected light form the toner patch on the transferring material to thereby find chromaticity, the accumulation time of the accumulation type sensor is changed in conformity with the reflectance of the toner patch, and even for a patch of small reflectance, the signal components are made great and then read and therefore, the influence of the quantization error during AD conversion or the noise of the reading-out circuit can be reduced, and irrespective of the reflectance of the patch, color measurement of high accuracy becomes possible.

Also, the amount of light of the light source is not changed and therefore, when the amount of light is to be changed, it is unnecessary to wait for color measurement until the amount of light becomes stable, and it is possible to increase the number of detectable patches for the limited length of the transferring material. In other words, controlling the accumulation time enables even a toner patch of low reflectance to be read at a great signal level, and enables detection good in S/N and reduced in the influence of the quantization error or the noise of the circuit to be accomplished.

Accordingly, when the present color measuring apparatus is carried on the color image forming apparatus and the chromaticity obtained from the toner patch is to be fed back to the image forming condition, feedback can be applied on the basis of the information from more patches, and an image of a more stable hue can be obtained.

Further, the accumulation time of the accumulation type sensor of the color measuring apparatus and the length of the toner patch in the conveyance direction are controlled in conformity with the reflectance predicted from the forming condition of the toner patch, and specifically in a color measuring apparatus for detecting the reflected light from the toner patch on the transferring material to thereby find chromaticity, when the accumulation time of the accumulation type sensor is changed in conformity with the reflectance of the toner patch, the length of the toner patch is also changed, namely, is controlled, in conformity with the reflectance, thereby to prevent the color mixing with the adjacent toner patch when color measurement is effected with the accumulation time extended, and also the length of the transferring material can be effectively utilized accurately to detect as many toner patches as possible within the limited length of the transferring material.

Accordingly, even for a patch of low reflectance, the influence of the quantization error during AD conversion or the noise of the reading-but circuit can be reduced, and irrespective of the reflectance of the patch, not only color measurement of high accuracy becomes possible, but also the detection of still more toner patches becomes possible within the limited length of the transferring material.

Thereby, when the present color measuring apparatus is carried on the color image forming apparatus and the chromaticity obtained from the toner patch is to be fed back to the image forming condition, feedback can be applied on the basis of the information from more patches, and an image of a more stable hue can be obtained.

Also, the amount of light of the light source of the color measuring apparatus and the accumulation time of the accumulation type sensor are controlled in conformity with the reflectance predicted from the forming condition of the toner patch and the actually measured reflectance (signal level) of the patch, and therefore, changing the color measuring condition in conformity with the actually measured reflectance of the patch enables the toner patch to be accurately color-measured even if the image forming condition deviates form the normal state.

Specifically, in a color measuring apparatus for detecting the reflected light from the toner patch on the transferring material to thereby find chromaticity, color measurement is effected with the measuring condition changed depending on not only the forming condition of the toner patch, but also the actually measured intensity of the reflected light from the patch, and therefore, even if the image forming condition of the toner patch deviates from the normal state, irrespective of the reflectance of the toner patch, there is obtained a sufficient signal amplitude difficult to be affected by the quantization error or the noise of the reading-out circuit and thus, color measurement of good accuracy becomes possible.

As described above, there is achieved the effect that the amount of reflected light is detected with the color measuring condition changed in adaptation to the reflectance predicted from the forming condition of color images to be detected, and the image forming condition is adjusted from the amount of reflected light of each of the detected color images, and therefore, irrespective of the reflectance of each color image, the color measurement of each color image is accurately effected to thereby accurately detect the hues and density of the color images to be detected, and a color image excellent in color reproducibility can be formed.

While the present invention has been described above with respect to some preferred embodiments thereof, it is apparent that the present invention is not restricted to these embodiments, but various modifications and applications are possible within the scope of the invention defined in the appended claims.

What is claimed is:

1. A color image forming apparatus comprising:
   an image forming unit which forms a color image on a recording material;
   a color measuring unit which optically measures each of colors of a plurality of patch images formed on a recording material by said image forming unit, by detecting each of reflected lights from the plurality of patch images;
   a measuring condition controller which variably sets a measuring condition of said color measuring unit in accordance with a patch image to be measured; and
   a forming condition controller which controls an image forming condition on a basis of a measuring result of said color measuring unit.

2. A color image forming apparatus according to claim 1, wherein said color measuring unit illuminates the plurality of patch image when said color measuring unit measures each of colors of a plurality of patch images, and the measuring condition is an amount of light of the light source.

3. A color image forming apparatus according to claim 2, wherein an amount of light of the light source as the measuring condition is variable so as to be decreased as a predicted reflectance becomes greater and to be increased as a predicted reflectance becomes smaller.

4. A color image forming apparatus according to claim 1, wherein said color measuring unit has an accumulation sensor which accumulates a reflected light from the plurality of patch image, and the measuring condition is an accumulation time of the accumulation sensor.

5. A color image forming apparatus according to claim 4, wherein the accumulation time as the measuring condition is variable so as to be decreased as a predicted reflectance becomes greater, and to be increased as a predicted reflectance becomes smaller.

6. A color image forming apparatus according to claim 4, wherein said image forming unit varies lengths of the plurality of patch images along a conveyance direction in accordance with the accumulation time.

7. A color image forming apparatus according to claim 6, wherein the length of the patch image varied along the conveyance direction as the measuring condition is shortened as a predicted reflectance becomes greater, and is lengthened as a predicted reflectance becomes smaller.

8. A color image forming apparatus according to claim 1, wherein said color measuring unit is provided with a light source having a spectrum over an entire visible light and a sensor having pixels provided with three or more filters having a spectral characteristic.

9. A color image forming apparatus according to claim 1, wherein said color measuring unit is provided with three or more light sources having difference spectra and one or more sensors.

10. A color image forming apparatus according to claim 1, wherein said color measuring unit is provided with a light source having a spectrum over an entire visible light and a sensor having means for separating the reflected light from the images and a plurality of pixels for measuring the intensity of the separated lights.

11. A color image forming apparatus according to claim 1, wherein said color measuring unit is provided with three or more light sources having different spectra, and one or more sensors, and when said light sources are turned on one by one and reflected lights corresponding to the respective light sources are detected by the sensor or sensors, the amount of light of each light source is varied in conformity with a predicted spectral reflectance.

12. A color image forming apparatus according to claim 1, wherein said measuring condition controller, when it sets the measuring condition, effects the setting of the measuring condition in conformity with an actually measured reflectance of the images.

13. A color image forming apparatus according to claim 1, wherein said color image forming apparatus further comprises a fixing unit that effects fixation an image on a recording material formed by said image forming unit, and said color measuring unit measures executes said each of colors of a plurality of patch images after the fixation.

14. A color image forming apparatus according to claim 1, wherein said color measuring unit has a converter that converts an analog output signal of an optical sensor to a digital signal.

15. A color image forming apparatus according to claim 1, wherein the patch image is made of mixed colors.

16. A color measurement controlling method for forming a color image on a recording material, comprising:
   an image forming step, of forming a plurality of a color image on a recording material;

a setting step, of variably setting a measuring condition of said color measuring step in accordance with a patch image to be measured;

a color measuring step of optically measuring each of colors of a plurality of patch images formed on a recording material in said image forming step, by detecting each of reflected lights from the plurality of patch images; and a controlling step, of controlling an image forming condition on a basis of a measuring result in said color measuring step.

17. A color measurement controlling method according to claim 16, wherein the plurality of patch images are illuminated when each of colors of a plurality of patch images is measured in said color measuring step, and the measuring condition is an amount of light of the light source.

18. A color measurement controlling method according to claim 17, wherein an amount of light of the light source as the measuring condition is variable so as to be decreased as a predicted reflectance becomes greater and to be increased as a predicted reflectance becomes smaller.

19. A color measurement controlling method according to claim 16, wherein in said color measuring step, an accumulation sensor is used for accumulating of a reflected light from the plurality of patch image, and the measuring condition is an accumulation time of the accumulation sensor.

20. A color measurement controlling method according to claim 19, wherein the accumulation time as the measuring condition is variable so as to be decreased as a predicted reflectance becomes greater, and to be increased as a predicted reflectance becomes smaller.

21. A color measurement controlling method according to claim 16, wherein in said image forming step, lengths of the plurality of patch images are varied along a conveyance direction in accordance with the accumulation time.

22. A color measurement controlling method according to claim 21, wherein the length of the patch image varied along the conveyance direction as the measuring condition is shortened as a predicted reflectance becomes greater, and is lengthened as a predicted reflectance becomes smaller.

23. A color measurement controlling method according to claim 16, wherein in said color measuring step, the optically measuring each of colors of a plurality of patch images is executed by a light source having a spectrum over an entire visible light and a sensor having pixels provided with three or more filters having a spectral characteristic.

24. A color measurement controlling method according to claim 16, wherein in said color measuring step, the optically measuring each of colors of a plurality of patch images is executed by three or more light sources having different spectra, and one or more sensors.

25. A color measurement controlling method according to claim 16, wherein in said color measuring step, the optically measuring each of colors of a plurality of patch images is executed by a light source having a spectrum over an entire visible light and a sensor having means for separating the reflected light from the images and a plurality of pixels for measuring the intensities of the separated lights.

26. A color measurement controlling method according to claim 16, wherein in said color measuring step, the optically measuring each of colors of a plurality of patch images is executed by three or more light sources having different spectra and one or more sensors, and said color measuring step includes a step of turning on the light sources one by one and changing the amount of light of each light source in conformity with the predicted spectral reflectance when the reflected lights corresponding to the respective light sources are detected by the sensor or sensors.

27. A color measurement controlling method according to claim 16, wherein in case of the setting of the detecting condition in said setting step, the setting of detecting the measuring condition is effected in conformity with an actually measured reflectance of the images.

28. A color image forming method according to claim 16, further comprising a fixing step, of fixing an image on a recording material formed in said image forming step, and wherein in said color measuring step, the optically measuring each of colors of a plurality of patch images is executed after said fixing step.

29. A color image forming method according to claim 16, wherein said color measuring step includes a step of converting an analog output signal of an optical sensor to a digital signal.

30. A color image forming method according to claim 16, wherein the patch image is made of mixed colors.

* * * * *

UNITED STATES PATENT AND TRADEMARK OFFICE
CERTIFICATE OF CORRECTION

PATENT NO. : 7,111,784 B2
APPLICATION NO. : 10/772359
DATED : September 26, 2006
INVENTOR(S) : Toshiki Nakayama It is certified that error appears in the above-identified patent and that said Letters Patent is hereby corrected as shown below:

ON THE TITLE PAGE ITEM [74]:

Insert --(74) Attorney, Agent, or Firm — Fitzpatrick, Cella, Harper & Scinto--.

COLUMN 3:

Line 26, "driven" should read --driven by--; and
Line 60, "affixing" should read --a fixing--.

COLUMN 12:

Line 3, "reflectance" should read --reflectance.--.

COLUMN 18:

Line 15, "form" should read --from--; and
Line 60, "reading-but" should read --reading-out--.

COLUMN 19:

Line 13, "form" should read --from--; and
Line 62, claim 2 "image" should read --images--.

COLUMN 20:

Line 6, claim "image," should read --images,--;
Line 29, claim "difference" should read --different--;
Line 53, claim 13 "fixation" should read --fixation of--;
Line 55, claim 13 "executes" should be deleted;
Line 65, claim 16 "a" (second occurrence) should be deleted; and
Line 66, claim 16 "image" should read --images--.

COLUMN 21:

Line 4, claim 16 "step" should read --step,--;
Line 24, claim 19 "of" should be deleted; and
Line 25, claim 19 "image," should read --images,--.

UNITED STATES PATENT AND TRADEMARK OFFICE
CERTIFICATE OF CORRECTION

PATENT NO. : 7,111,784 B2
APPLICATION NO. : 10/772359
DATED : September 26, 2006
INVENTOR(S) : Toshiki Nakayama It is certified that error appears in the above-identified patent and that said Letters Patent is hereby corrected as shown below:

COLUMN 22:

Line 27, claim 27 "detecting" should be deleted.

Signed and Sealed this

Twentieth Day of March, 2007

JON W. DUDAS
*Director of the United States Patent and Trademark Office*